United States Patent
Murray et al.

(10) Patent No.: US 7,354,606 B2
(45) Date of Patent: Apr. 8, 2008

(54) NUTRITIONAL SUPPLEMENT CONTAINING ALPHA-GLUCOSIDASE AND ALPHA-AMYLASE INHIBITORS

(75) Inventors: Mary A. Murray, Irvine, CA (US); James B. Roufs, Santa Monica, CA (US); Haeri Roh-Schmidt, Ada, MI (US)

(73) Assignee: Access Business Group International LLC, Ada, MI (US)

( * ) Notice: Subject to any disclaimer, the term of this patent is extended or adjusted under 35 U.S.C. 154(b) by 203 days.

(21) Appl. No.: 11/131,538

(22) Filed: May 18, 2005

(65) Prior Publication Data

US 2005/0208161 A1   Sep. 22, 2005

Related U.S. Application Data

(62) Division of application No. 10/290,079, filed on Nov. 7, 2002, now Pat. No. 7,108,869.

(51) Int. Cl.
*A01N 65/00* (2006.01)
(52) U.S. Cl. .................................... 424/725
(58) Field of Classification Search ............... None
See application file for complete search history.

(56) References Cited

U.S. PATENT DOCUMENTS

| | | | |
|---|---|---|---|
| 3,934,006 A | 1/1976 | Frommer et al. | |
| 3,950,319 A | 4/1976 | Schmidt et al. | |
| 4,010,258 A | 3/1977 | Murao | |
| 5,093,315 A | 3/1992 | Maeda et al. | |
| 5,322,697 A | 6/1994 | Meyer | |
| 5,637,324 A | 6/1997 | Bland | |
| 5,643,874 A | 7/1997 | Bremer et al. | |
| 5,753,253 A | 5/1998 | Meyer | |
| 6,200,958 B1 | 3/2001 | Odaka et al. | |
| 6,267,988 B1 | 7/2001 | Meyer | |
| 6,299,911 B1 * | 10/2001 | Kawabata et al. | 424/757 |
| 6,340,669 B1 | 1/2002 | Cestaro et al. | |
| 6,365,206 B1 | 4/2002 | Yanai et al. | |
| 6,376,549 B1 | 4/2002 | Fine et al. | |
| 6,399,101 B1 * | 6/2002 | Frontanes et al. | 424/488 |
| 2003/0004215 A1 | 1/2003 | Van Laere et al. | 514/557 |
| 2003/0059403 A1 * | 3/2003 | Chokshi | 424/93.3 |
| 2003/0059457 A1 | 3/2003 | Chokshi | 424/439 |
| 2003/0082168 A1 | 5/2003 | Yegorova | 424/94.61 |
| 2004/0018990 A1 | 1/2004 | Rosner | 514/25 |

FOREIGN PATENT DOCUMENTS

| | | | |
|---|---|---|---|
| EP | 1 157 696 A2 | 11/2001 | |
| JP | HEI 9-2963 | 6/1995 | |
| JP | A-2000-186044 | 7/2000 | |
| WO | WO 00/12080 | * | 3/2000 |
| WO | WO 01/17369 | | 3/2001 |

OTHER PUBLICATIONS

L. Quarino, J. Hess, M. Shenouda, R.R. Ristenbatt, J. Gold, R.C. Shaler, J *Differentiation of Alpha-Amylase From Various Sources: An Approach Using Selective Inhibitors*, J. Forensic Sci Soc Apr.-Jun. 1993; 33(2): 87-94.

H. Fujita, T. Yamagami, K. Oshima, *Fermented Soybean-Derived Water-Soluble Touchi Extract Inhibits Alpha-Glucodase and is Antiglycemic in Rats and Humans Alter Single Oral Treatment*, J. Nutr Apr. 2001; 131(4): 1211-3.

H. Fujita, T. Yamagami, K. Oshima, *Long-Term Ingestion of a Fermented Soybean-Derived Touchi-Extract with Alpha-Glucosidase Inhibitory Activity is Safe and Effective in Human with Borderline and Mild Type-2 Diabetes*, J Nutr Aug. 2001; 131(8): 2105-8.

F. Hiroyuki, Y. Tomohide, O. Kazunori, *Efficacy and Safety of Touchi Extract, An Alpha-Glucosidase Inhiboitor Derived From Fermented Soybens, in Non-Insulin-Dependent Diabetic Mellitus*, J Nutr Biochem Jun. 2001; 12(6): 351-356.

H. Fujita, T. Yamagami,, *Fermented Soybean-Derived Touchi-Extract with Anti-Diabetic Effect Via Alpha-Glucosidase Inhibitory Action in a Long-Term Administration Study with KKAy Mice*, Life Sci Nov. 30, 2001; 70(2): 219-27.

http://www.advantagesupplements.com/advantagesupplements/bioculcarpha.html.
http://www.getbigger.com/jarrow.html.
http://www.iherbi.com/sn-1409.
http://www.iherbi.com/carb.html.
http://www.internetdietcenter.com/dynamicduo/html.

(Continued)

*Primary Examiner*—Michael Meller
(74) *Attorney, Agent, or Firm*—Brinks Hofer Gilson & Lione

(57) ABSTRACT

A nutritional supplement composition contains inhibitors of alpha-glucosidase and alpha-amylase substantially in the absence of lipase inhibitors. The composition can include touchi extract and phaseolamin as the alpha-glucosidase and alpha-amylase inhibitor, respectively. A method of limiting the absorption of carbohydrates contained in a foodstuff includes administering the nutritional supplement composition prior to consumption of the carbohydrates, and a method promoting weight loss in an individual includes administering the nutritional supplement composition to the individual over a period of days.

12 Claims, No Drawings

OTHER PUBLICATIONS http://www.lifevigor.com/products/512101.html.
http://www.masonvitamins.com/new%20body/carbo.htm.
http://www.pennherb.com/pennherb/info/scan54.html.
http://www.primev.com/pro701205.htm.
Touchi, http://www.nippon-sapuri.com/english/touchi.html, Nippon Supplement, Inc.
Abstract: *Nutraceutical resources for diabetes prevention—an update*, McCarty Mark F, NutriGuard Research, (Encinitas, Cal., USA) Medical hypotheses, (Scotland) 2005 64 (1) 151-8, ISSN 0306-9877 Journal Code: 7505668.
Abstract: *Current and emerging therapies for type 2 diabetes*, BioMinerva (San Diego, Cal., USA) IDrugs 7, No. 3, 249-56, 2004.
Abstract: *Orlistat augments postprandial increases in glucagons-like peptide 1 in obese type 2 diabetic patients*, Damci Taner; Yalin Serap; Bbalci Huriye; Osar Zeynep; Korugan Ustun; Ozyazar Mucahit; Ilkova Hasan, Istanbul University Cerrahpasa Medical School, Department of Internal Medicine, Division of Endocrinology Diabetes and Metabolism, Istanbul, Turkey: Istanbul University Cerrahpasa Medical School, Central Laboratories (Istanbul, Turkey) Journal: Diabetes care, 2004, 27 (5) 1077-1080.
Abstract: *Oral antidiabetic drugs in 2003*, Ducobu J, Service de Medecine Interne, C.H.U. Tivoli, La Louviere, U.L.B. Revue medicale de Bruxelles (Belgium) Sep. 2003, 24 (4) 361-8, ISSN 0035-3639 Journal Code: 8003474.
Abstract: *Alpha amylase is a major allergenic component in occupational asthma patients caused by porcine pancreatic extract*, Park Hae-Sim; Kim Hee-Yeon; Suh You Jin; Lee Soo-Jin; Lee Soo-Keol; Kim Sun-Sin; Nahm Dong-Ho, Department of Allergy and Clinical Immunology, Ajou University School of Medicine, Suwon, Korea, Journal of Asthma—official journal of the Association for the Care of Asthma (USA) Sep. 2002, 39 (6) 511-6, ISSN 0277-0903, Journal Code: 8106454.
Abstract: *Inhibitors of absorption as anti-obesity drugs*, Tsuji M; Saito N; Inoue S, First Department of Internal Medicine, Showa University, (Tokyo, Japan), Nippon yakurigaku zasshi, Japanese journal of pharmacology (Japan), Nov. 2001, 118 (6) 340-6,, ISSN 0015-5691, Journal Code: 0420550.
Abstract: *Oral Hypoglycemic agents: insulin secretagogues, alpha-glucosidase inhibitors and insulin sensitizers*, Raptis S.A.; Dimitraiadis G.D., 2nd Department of Internal Medicine, Research Institute and Diabetes Center, Athens University (Athens, Greece), Experimental and clinical endocrinology & diabetes—official journal, German Society of Endocrinology and German Diabetes Association (Germany) 2001, 109 Suppl 2 265-87, ISSN 0947-7349, Journal Code: 9505926.
Abstract: *Drug-induced diarrhoea*, Chassany O; Michaux A; Bergmann J F, Internal Medicine Department, Lariboisiere University Hospital, Paris, France, Drug safety—an international journal of medical toxicology and drug experience (New Zealand), Jan. 2000, 22 (1) 53-72, ISSN 0114-5916, Journal Code: 9002928.

Abstract: *The selective inhibition of intestinal enzymes, a new therapeutic concept*, Scheen A.J.; Letiexhe M.M.; Paquot N.; Lefebvre P.J.; Prof. A.J. Scheen, Serv Diabetol, Nutr./Malad. Metabool, Department de Medicine, CHU Sart Tilman (Liege, Belgium), Medicine et hygiene (Switzerland), Aug. 25, 1999, 57/2265, 1521-1525, ISSN 0025-6749, Journal Review.
Abstract: *Pharmacological treatment of obesity: Present status*, Scheen A.J.; Lefebvre P.J., Prof. A.J. Scheen, Division of Diabetes, (Belgium), International Jouranl of Obesity (U.K.), 1999, 23/Suppl. 1 47-53, ISSN 0307-0565, Journal, Conference Paper.
Abstract: *Intestine as a target for the pharmacological treatment of metabolic diseases*, Scheen, A.J., Department de Medicine, (Belgium), Revue Medicale de Liege 1998, 53/11, 646-650, ISSN 0035-3663, Journal Article.
Abstract: *Effect of acarbose on postprandial lipid metabolism in type 2 diabetes mellitus*, Kado S.; Murakami T; Aoki A; Nagase T; Katsura Y; Noritake M.; Matsuoka T; Nagata N, (Tokyo, Japan), Diabetes Research and Clinical Practice, Jul. 1998, V41, N1 49-55, ISSN: 0168-8227, Article.
Abstract: *Type 2 diabetes: new therapeutic perspectives*, Bouhanick B; Berrut G; Fressinaud P; Marre M, Service de Medeicine B, Centre Hospitalier et Universitaire d'Angeres (France), Dec. 12, 1998, 27 (39), 2015-24, ISSN 0755-4982, Journal Code: 8302490.
Abstract: *Drug clinics. How I treat various metabolic diseases treated by a drug intervention that targets the intestine*, Scheen, A.J.; Department de Medecine, (Belgium), Nov. 1998, 53 (11) 646-50, ISSN 0370-629X, Journal Code: 0404317.
Abstract: *Management of obesity in NIDDM (non-inselin-dependent diabetes mellitus)*, Cheah J.S., Department of Medicine, National University Hospital, (Singapore), Aug. 1998, 39 (8), 380-4, ISSN 0037-5675, Journal Code 0404516.
French Abstract: *Diabete de type 2: nouveautes en therapeutique*, Bouhanick B; Berrut G; Fressinaud P; Marre M, Service de Medecine B, (Angers, France), Journal: La Presse medicale: (1983), 1998, 27 (39) 2015-2023, ISSN: 0755-4982.
Abstract: *Modification of Energy Density with Inhibitors of Carbohydrate and Fat*, Taylor, R.H., Proc. Nutr. Soc 50, No. 2, 399-408, 1991.
Abstract: *Mechanism of Action of Aflatoxin B-1*, Tiwar R P; Bhalla T C; Saini S S; Singh G; Vadehra D V, Dep. of Microbial (India), Journal of Biosciences (Bangalore) 10 (1): pp. 145-152, 1986, ISSN: 0250-5991.
Abstract: *Reduction of carbohydrate-induced hypertriglyceridemia in (fa, fa) 'Zuker' rats by the alpha-glucosidase inhibitor acarbose (BAY g 5421)*, Krause H.P.; Keup U; Thomas G; Puls W.; Metabolism-clinical and experimental (USA), Jul. 1982, 31 (7) 710-4, ISSN 0026-0495, Journal Code 0375267, Journal Article.

* cited by examiner

NUTRITIONAL SUPPLEMENT CONTAINING ALPHA-GLUCOSIDASE AND ALPHA-AMYLASE INHIBITORS

RELATED APPLICATIONS

This application is a divisional of U.S. application Ser. No. 10/290,079, filed Nov. 7, 2002 now U.S. Pat. No. 7,108,869, which is hereby incorporated by reference.

BACKGROUND OF THE INVENTION

The present invention relates to nutritional supplement compositions containing alpha-glucosidase and alpha-amylase inhibitors. More specifically, the invention relates to nutritional supplement compositions that include effective amounts of alpha-glucosidase and alpha-amylase inhibitors substantially in the absence of lipase inhibitor. The present invention also relates to methods of limiting the absorption of carbohydrates contained in a foodstuff, and to methods of promoting weight loss in an individual.

Carbohydrates are nutritional compounds that are present in a wide array of foodstuffs. They are a group of numerous different compounds that occur in a variety of sizes and configurations. All carbohydrates are composed of one or more sugar units linked together through glycosidic bonds. Complex carbohydrates, such as starch, are relatively large molecules consisting of numerous repeating units formed into a multi-branched chain structure. Monosaccharides and disaccharides, on the other hand, are simple carbohydrates that comprise single and double sugar units, respectively.

The human body digests complex carbohydrates by breaking them into relatively simple units, monosaccharides, and then absorbing these units into a tissue, such as the intestine. A variety of digestive enzymes work in a stepwise manner to break the complex carbohydrates into the absorbable units. In an initial step, salivary and pancreatic enzymes known as amylases break large carbohydrates into smaller units of oligo- and disaccharides. In one of the final steps of carbohydrate digestion, alpha-glucosidase enzymes in the brush border of the small intestine break the disaccharides maltose and sucrose into their respective monosaccharide units, which can then be absorbed by the body.

A balanced diet includes several types of nutritional compounds, including carbohydrates. Recent suggestions indicate that a disproportionate level of carbohydrates in the diet, however, may contribute to obesity. As a result, several types of low- and no-carbohydrate foods and diets have been proposed.

Considering the prevalence of carbohydrates in many diets throughout the world, it is difficult for an individual to avoid carbohydrates. Furthermore, an individual interested in losing weight may not be willing to sacrifice the enjoyment of carbohydrate-containing foods. As a result, considerable attention has been focused on finding alternatives to the reduction and/or elimination of carbohydrates from the diet.

The enzymes that digest carbohydrates into absorbable units present opportunities to prevent the absorption of these compounds. By inhibiting the function of the appropriate enzymes, carbohydrates will not be broken into their absorbable units and will pass through the body unabsorbed. This allows an individual to enjoy carbohydrate-containing food while still avoiding the absorption of carbohydrates.

The art has several examples of compositions that prevent the absorption of carbohydrates. For example, U.S. Pat. No. 6,200,958 to Odaka et al. discloses a composition that includes an alpha-glucosidase inhibitor. The composition is used to retard the digestion of carbohydrates such as starch and sucrose. U.S. Pat. No. 5,643,874 to Bremer et al. discloses a nutritional supplement composition that contains a glucosidase inhibitor and/or an amylase inhibitor in the presence of a lipase inhibitor. The composition prevents the absorption of carbohydrates, and can be used in the treatment of obesity: The '874 patent teaches that the presence of the lipase inhibitor is critical to the function of the composition.

While the art includes these and other examples of compositions that limit the absorption of carbohydrates, there remains a need for compositions having improved abilities to prevent such absorption.

SUMMARY OF THE INVENTION

The present invention includes a nutritional supplement composition having an alpha-glucosidase inhibitor and an alpha-amylase inhibitor substantially in the absence of lipase inhibitor. The inventors discovered that the combination of an alpha-glucosidase inhibitor with an alpha-amylase inhibitor, substantially in the absence of a lipase inhibitor, provides an effective inhibitor of carbohydrate absorption. Compositions according to the invention are particularly useful in limiting the absorption of carbohydrates contained in a foodstuff, and in promoting weight loss.

The inventors discovered, surprisingly, that the combination of a touchi extract, an alpha-glucosidase inhibitor, and phaseolamin, an alpha-amylase inhibitor, produces a synergy that enables nutritional supplement compositions according to the present invention to block carbohydrate absorption more effectively than expected. Touchi is a traditional Chinese food primarily used as a seasoning in the form of paste. Touchi is derived from steamed soybeans fermented by koji, *Aspergillus* species fungi. The touchi used in the nutritional supplement compositions of the present invention is an extract of touchi. Desirably, the touchi extract is a water extract.

In desirable embodiments, nutritional supplement compositions according to the present invention include an extract of touchi in an amount between about 7 and 35 weight percent of the composition. More desirable, the touchi extract is present in an amount between about 13 and 27 weight percent of the composition. Particularly desirable, the touchi extract is present in an amount between about 18 and 19 weight percent of the composition.

Phaseolamin is a partially-purified protein extract of white kidney beans (*Phaseolus vulgaris*) that binds to alpha-amylase enzymes, which are responsible for the digestive breakdown of starch. It has been proposed that phaseolamin inhibits the alpha-amylase breakdown of starch by non-competitively binding the enzyme to prevent the hydrolysis of the alpha-1,4-glycosidic linkages in the starch molecule.

In desirable embodiments, nutritional supplement compositions according to the present invention include phaseolamin in an amount between about 15 and 48 weight percent of the composition. More desirable, the phaseolamin is present in an amount between about 24 and 40 weight percent of the composition. Particularly desirable, the phaseolamin is present in an amount between about 31 and 32 weight percent of the composition.

Particularly desirable nutritional supplement compositions according to the present invention comprise solid dosage units individually comprising about 100 mg touchi extract and about 166.67 mg phaseolamin.

Compositions according to the present invention may further comprise a carminative. In a desirable embodiment, organic parsley is used as the carminative.

The present invention also provides a method of limiting the absorption of carbohydrates present in a foodstuff. The method comprises administering to an individual a nutritional supplement composition according to the invention. In a desirable method, the administering is done at a time point prior to the consumption of the carbohydrates by the individual. In a more desirable method, the administering is done between 1 second and 30 minutes before the consumption of the carbohydrates. In a still more desirable method, the administering is done between 10 and 25 minutes before the consumption of the carbohydrates. In a particularly desirable method, the administering is done at about 15 minutes before the consumption of the carbohydrates.

The present invention also provides a method of promoting weight loss in an individual. The method comprises repeatedly administering a nutritional supplement composition to an individual over a period of time. In a desirable method, the composition is administered once daily for a period of between about 4 and 52 weeks. In another desirable method, the composition is administered with carbohydrate-containing meals multiple times daily for a period of about 1 month.

DETAILED DESCRIPTION OF DESIRABLE EMBODIMENTS OF THE INVENTION

While the invention is defined by the claims appended hereto, additional understanding of the invention can be obtained from the following description of desirable embodiments. The description is not intended to limit the scope of the invention, but rather serves to enable those possessing ordinary skill in the relevant art to make and use the present invention.

In accordance with the present invention, a nutritional supplement composition comprises an effective amount of an alpha-glucosidase inhibitor and an effective amount of an alpha-amylase inhibitor. The nutritional supplement composition may contain an acceptable carrier for nutritional supplements.

The nutritional supplement composition is substantially free of lipase inhibitor. As used herein, the term "substantially free of lipase inhibitor" means that the composition contains only any amount of a lipase inhibitor that is present by way of acceptable contamination, or by any level of lipase inhibitory activity exhibited by the alpha-glucosidase and/or alpha-amylase components. Desirably, any lipase inhibitor present by way of acceptable contamination (i.e., exclusive of the alpha-glucosidase and alpha-amylase inhibitors) comprises less than 0.001 weight percent of the nutritional supplement composition.

Alpha-glucosidase is an enzyme that breaks disaccharides into their respective monosaccharide units. Alpha-glucosidase inhibitors prevent the enzyme from performing this function. A wide variety of alpha-glucosidase inhibitors are known and any suitable inhibitor can be used in the compositions and methods of the present invention. Examples of suitable alpha-glucosidase inhibitors include, but are not limited to, voglibose (see U.S. Pat. No. 6,200,958 to Odaka et al.), acarbose (see U.S. Pat. No. 5,643,874 to Bremer et al.), and touchi extract.

In desirable embodiments, the alpha-glucosidase inhibitor comprises an extract of touchi. Touchi is a traditional Chinese food derived from soybeans. Touchi is prepared by first steaming and then fermenting soybeans with *Aspergillus* species bacteria. Typically, touchi is used for food purposes in a paste form. The touchi useful in the present invention is an extract of touchi. As used herein, the terms "touchi extract," and "extract of touchi," are "touchi" all refer to a touchi extract.

Any suitable touchi extract can be utilized in the present invention. The extract need only retain the desired inhibitory effect on alpha-glucosidase activity. A water extract of touchi is particularly desirable. U.S. Pat. No. 6,299,911 to Kawabata et al. describes suitable touchi extracts and methods of preparing the extracts, and is incorporated herein by reference in its entirety for the purpose of describing the applicable touchi extracts and their methods of preparation. Desirably, the touchi extract comprises a powder form of a water extract of touchi.

Nutritional supplement compositions according to the present invention comprise an effective amount of the alpha-glucosidase inhibitor. The effective amount utilized will depend on the desired inhibitory effect of the nutritional supplement composition. Desirably, the effective amount of alpha-glucosidase inhibitor comprises an amount able to block the absorption of a quantity of carbohydrates that might be obtained from a typical high carbohydrate meal. As used herein, the term 'high carbohydrate meal' is defined as meals containing more than about 80 grams of carbohydrates. Accordingly, the effective amount of alpha-glucosidase inhibitor desirably comprises an amount able to block the absorption of between about 60 and 100 grams of carbohydrate. Particularly desirable, the effective amount of alpha-glucosidase inhibitor desirably comprises an amount able to block the absorption of between about 70 and 90 grams of carbohydrate. Most desirable, the effective amount of alpha-glucosidase inhibitor comprises an amount able to block the absorption of about 80 grams of carbohydrate.

Alpha-amylase is an enzyme that functions to break the alpha-1,4-glycosidic linkages present in starch. This breaks the complex starch molecule into smaller units, such as disaccharides, that can be further digested by other enzymes, such as alpha-glucosidase. Alpha-amylase inhibitors prevent the enzyme from hydrolyzing the alpha-1,4-glycosidic bond, and therefore prevent the breakdown of starch. A wide variety of alpha-amylase inhibitors are known, and any suitable inhibitor can be used in the compositions and methods of the present invention. Examples of suitable alpha-amylase inhibitors include, but are not limited to, an inhibitor extracted from wheat (see U.S. Pat. No. 3,950,319 to Schmidt et al.), Amylostatin-A (see U.S. Pat. No. 4,010,258 to Murao), and phaseolamin.

In desirable embodiments, the alpha-amylase inhibitor comprises phaseolamin. Phaseolamin is an extract of the white kidney bean (*Phaseolus vulgaris*). The extract is water-soluble and rich in protein content. Phaseolamin is readily available from numerous commercial suppliers. Phaseolamin 2250®, available from Pharmachem Laboratories of Kearny, N.J. and also known as Phase 2, is a standardized extract particularly well-suited for inclusion in the compositions according to the present invention. This phaseolamin demonstrates a high ability to block alpha-amylase activity.

Nutritional supplement compositions according to the present invention comprise an effective amount of the alpha-amylase inhibitor. The effective amount utilized will depend on the desired inhibitory effect of the nutritional supplement composition. Desirably, the effective amount of alpha-amylase inhibitor comprises an amount able to block the breakdown of a quantity of starch that might be present in a typical, high carbohydrate foodstuff. Accordingly, the effective amount of alpha-amylase inhibitor desirably comprises an amount able to block the breakdown of between about 60 and 100 grams of starch. Particularly desirable, the effective amount of alpha-amylase inhibitor desirably comprises an amount able to block the breakdown of between about 70 and 90 grams of starch. Most desirable, the effective amount of alpha-amylase inhibitor comprises an amount able to block the breakdown of about 80 grams of starch.

The presence of both the alpha-glucosidase inhibitor and the alpha-amylase inhibitor in compositions of the present invention provides an effective blocker of carbohydrate digestion. Indeed, in a desirable embodiment containing touchi extract and phaseolamin, the composition is surprisingly more effective at blocking carbohydrate absorption than the ingredients acting individually (see Example 2). While not desiring to be limited to a particular mechanism, the inventors hypothesize that the two inhibitors act synergistically to enhance the capacity of each individual inhibitor.

The nutritional supplement compositions according to the present invention can further comprise one or more acceptable carriers. A wide number of acceptable carriers are known in the nutritional supplement arts, and the carrier can be any suitable carrier. The carrier need only be suitable for administration to animals, including humans, and be able to act as a carrier without substantially affecting the desired activity of the inhibitors. Also, the carrier(s) may be selected based upon the desired administration route and dosage form of the composition. For example, the nutritional supplement compositions according to the present invention are suitable for use in a variety of dosage forms, such as liquid form and solid form. In desirable embodiments, as discussed below, the nutritional supplement compositions comprise a solid dosage form, such as a tablet or capsule. Examples of suitable carriers for use in tablet and capsule compositions include, but are not limited to, organic and inorganic inert carrier materials such as gelatin, starch, magnesium stearate, talc, gums, silicon dioxide, stearic acid, cellulose, and the like. Desirably, the carrier is substantially inert, but it should be noted that the nutritional supplement compositions of the present invention may contain further active ingredients in addition to the alpha-glucosidase and alpha-amylase inhibitors.

In a desirable embodiment, silicified microcrystalline cellulose is utilized as a carrier. Silicified microcrystalline cellulose is a physical mixture of microcrystalline cellulose and colloidal silicon dioxide. A suitable form of silicified microcrystalline cellulose for use in the compositions of the present invention is Prosolve 90 available from Penwest of Patterson, N.J. Further silicon dioxide, in addition to that provided by the silicified microcrystalline cellulose, is advantageously added to the compositions of the present invention as a processing aid. For example, further silicon dioxide can be included as a glidant to improve the flow of powder during compression in the manufacturing of solid dosage units, such as tablets.

Other inert ingredients can be utilized, such as lubricants and/or glidants, in the compositions according to the present invention. Lubricants ease the handling of tablets during manufacturing, such as during ejection from dies, and glidants improve powder flow during tablet compression. Stearic acid is an acceptable lubricant/glidant for use in the nutritional supplement compositions according to the present invention.

Example 1 provides a particularly desirable formulation for a composition according to the present invention.

The nutritional supplement compositions of the present invention are advantageously made in solid dosage form, such as tablets and capsules. This form provides a product that can be easily transported with an individual to a place of eating, such as a restaurant, and taken prior to consumption of a foodstuff. Also, the compositions are advantageously formulated into dosage units that contain suitable amounts of the inhibitors that permit an individual to determine an appropriate number of units to take based upon appropriate parameters, such as body weight, foodstuff size, and carbohydrate content.

The alpha-glucosidase inhibitor and alpha-amylase inhibitor are desirably present in the nutritional supplement composition in a weight ratio (of these two ingredients only) between about 5-95% alpha-glucosidase inhibitor and between about 95-5% alpha-amylase inhibitor. More desirable, these ingredients are present in a weight ratio between about 10 and 45% alpha-glucosidase inhibitor and between about 55 and 90% alpha-amylase inhibitor. Particularly desirable, these ingredients are present in a weight ratio of about 16% alpha-glucosidase inhibitor and about 84% alpha-amylase inhibitor.

The alpha-glucosidase inhibitor and alpha-amylase inhibitors are desirably present in the nutritional supplement composition as a weight percentage of the entire composition between about 7 and 35% alpha-glucosidase inhibitor and between about 15 and 48% alpha-amylase inhibitor. More desirable, the alpha-glucosidase inhibitor is present as between about 13 and 27 weight percentage of the composition, and the alpha-amylase inhibitor is present as between about 24 and 40% weight percentage of the composition. Still more desirable, the alpha-glucosidase inhibitor comprises between about 17 and 20 weight percentage of the composition, and the alpha-amylase inhibitor comprises between about 29 and 34 weight percentage of the composition. In one embodiment, the alpha-glucosidase inhibitor comprises touchi extract present as between about 18 and 19 weight percentage of the composition and the alpha-amylase inhibitor comprises phaseolamin present as between about 31 and 32 weight percentage of the composition.

In a particularly desirable embodiment, the nutritional supplement composition according to the present invention comprises solid tablets individually comprising between about 10 and 3,000 mg touchi extract and between about 70 and about 4,500 mg phaseolamin. Even more desirable, the nutritional supplement comprises solid tablets individually comprising between about 100 and 1000 mg touchi extract and between about 100 and 500 mg phaseolamin. Particularly desirable, the nutritional supplement comprises solid tablets individually comprising about 100 mg touchi extract and about 166.67 mg phaseolamin. As indicated above, it is especially desirable that these quantities represent between about 18 and 19 weight percent of the nutritional supplement composition, and between about 31 and 32 weight percent of the composition, respectively. This dosage composition provides a level of inhibitory effect in a single unit that may be effective for some individuals and/or some foodstuffs, and also allows for relatively simple dosage increases to provide other levels of inhibitory effects that may be effective for other individuals and/or other foodstuffs. For example, a three tablet dose of this desirable embodiment provides about 300 mg touchi and about 500 mg phaseolamin. These amounts, as indicated in the Examples, may be able to block up to 500 kilocalories, or 100 grams, of carbohydrates.

The nutritional supplement compositions according to the present invention can advantageously contain one or more carminatives, which act as soothing agents. A wide variety of carminatives are known in the nutritional supplement arts, and any suitable carminative can be utilized in the present invention. The selection of a carminative will depend on the desired characteristics of the nutritional supplement composition. For example, it may be desirable for the composition to have a certain texture, appearance, or taste. Also, the carminative can serve an additional function, such as providing nutrients. If present, the carminative desirably comprises between about 0.01 and about 3 weight percent of the nutritional supplement composition. Suitable organic parsley is readily available from a variety of commercial sources.

Organic parsley is a desirable carminative for use in the compositions according to the present invention. Organic parsley provides a desirable appearance to the composition, and also contributes to a desirable taste. Furthermore, organic parsley is known to help prevent gas formation in the gastrointestinal tract. The formation of gas in the gastrointestinal tract has been associated with various compositions for inhibiting absorption of various compounds. Thus, the inclusion of organic parsley in the nutritional supplement compositions of the present invention makes these compositions more desirable. Additionally, organic parsley confers further benefit by providing trace amounts of key nutrients, such as B vitamins (e.g., thiamin, riboflavin, niacin, folate, and vitamin B6), vitamin C, and Vitamin E, as well as minerals such as calcium, chromium, copper, iron, magnesium, manganese, molybdenum, potassium, selenium, zinc, and others. Also, parsley contains phytochemicals with antioxidant properties such as beta-carotene, lutein, quercetin, rosmarinic acid, and others.

The present invention also provides a method of limiting the absorption of carbohydrates contained in a foodstuff. The method comprises administering to an individual a nutritional supplement composition comprising an effective amount of an alpha-glycosidase inhibitor and an effective amount of an alpha-amylase inhibitor substantially in the absence of a lipase inhibitor. Desirably, the method comprises administering a nutritional supplement comprising an effective amount of a touchi extract and an effective amount of phaseolamin substantially in the absence of lipase inhibitor.

The nutritional supplement compositions according to the present invention inhibit the activity of carbohydrate digestive enzymes. For carbohydrate-conscious eaters, it may be desirable to accomplish this inhibition prior to the consumption of a high carbohydrate foodstuff, or prior to the consumption of a typical foodstuff. This may allow the inhibitors to limit the absorption of carbohydrates contained in a particular foodstuff. The administering can be conducted at a time point prior to the consumption of the foodstuff of interest, simultaneously with consumption of the carbohydrates, or after completion of consumption of the carbohydrates. Desirably, the composition is administered between about 1 second and 30 minutes prior to consumption of the carbohydrates. More desirably, the composition is administered between about 10 and 25 minutes prior to consumption of the carbohydrates. More desirably, the composition is administered approximately 15 minutes prior to consumption of the carbohydrates. The actual time point chosen will depend on several factors, including the dosage of nutritional supplement composition being utilized.

The inventors have discovered, surprisingly, that the nutritional supplement compositions according to the present invention are effective in promoting weight loss. This occurs despite the absence of a lipase inhibitor in the compositions. Without limiting the present invention to a particular mechanism of action, the inventors believe this effect arises due to the presence of phaseolamin, which has been shown to promote over a 5 pound weight loss and over a 10% body fat loss in a one month period. Thus, the present invention provides nutritional supplement compositions that inhibit the activity of relevant carbohydrate digestive enzymes and promote weight loss, all substantially in the absence of a lipase inhibitor. This enables the compositions to be used as pre-meal carbohydrate blocker, a weight loss promoter, or both.

Accordingly, the present invention also provides a method of promoting weight loss in an individual. The method comprises administering to an individual over a period of days a nutritional supplement composition comprising an effective amount of alpha-glycosidase inhibitor and an effective amount of an alpha-amylase inhibitor substantially in the absence of a lipase inhibitor. Desirably, the method comprises administering a nutritional supplement comprising an effective amount of a touchi extract and an effective amount of phaseolamin substantially in the absence of lipase inhibitor. In a particularly desirable method, the administering comprises administering the composition in solid dosage units that individually comprise about 100 mg touchi and about 166.67 mg phaseolamin. In another particularly desirable method, the administering comprises administering the composition once daily for a period of between about 4 and about 52 weeks. In other desirable methods, the administering comprises administering the composition once daily for a period of 1 month. In other desirable methods, the composition is administered at each carbohydrate-containing meal over a period of days, such as between 2 days and 52 weeks.

EXAMPLES

Example 1

The nutritional supplement composition according to the present invention was formed into single dosage tablets containing the following ingredients at the indicated amounts and percentages:

TABLE I

| Ingredient | Quantity (mg) | Weight percent of total composition |
|---|---|---|
| Silicified microcrystalline cellulose | 215 | 40.71 |
| Touchi Extract | 100 | 18.93 |
| Modified Cellulose Gum (croscarmellose sodium), a tablet disintegrant | 12.5 | 2.37 |
| Phaseolamin | 166.67 | 31.56 |
| Stearic acid | 20 | 3.79 |
| Silicon dioxide | 4 | 0.76 |
| Organic parsley | 10 | 1.89 |

In this form, the composition provides the desired inhibitory effects and allows for relatively easy dosage increases based on various parameters, such as meal size, carbohydrate content, and body weight. For example, a three tablet dose will contain about 300 mg touchi and about 500 mg phaseolamin.

Example 2

Methods for Determination of Enzyme Inhibition
Three materials (Touchi (Soybean extract), Phaseolamin (white kidney bean extract) and the composition according to Example 1) were tested for their inhibitory effects on alpha-glucosidase (AGH) and alpha-amylase activity. Using an assay that is modified from a known assay (Bernfeld, P., Amylases, alpha and beta in Methods in Enzymology, Vol. I, (Colowick, S. P., and Kaplan, N. O., eds.) pg 149, Academic Press, New York (1955), the inventors evaluated kilocaloric (kcal) blocking potential of touchi extract alone, phaseolamin alone, and the composition of Example 1.

Sample Calculations for Units of Enzyme Inhibited and Carbohydrate Inhibiting Potential as kcal In brief, standard alpha-glucosidase or alpha-amylase were used to generate standard calibration of enzyme activity by measuring formation of the product (i.e., glucose in the case of alpha-glucosidase activity or maltose in the case of alpha-amylase activity) from the appropriate substrate. Enzyme inhibition exerted by touchi extract or phaseolamin was determined by using maximum amount of enzyme from the calibration curve and measuring resulting activity that was decreased due to the presence of the touchi or phaseolamin. A similar method was used to determine alpha-glucosidase and alpha-amylase inhibition in the composition.

A synergy towards inhibition of both enzymes was determined from the composition, when unexpectedly higher inhibition of both alpha-glucosidase and alpha-amylase activity was observed compared to theoretical values derived from calculation of units of enzymes inhibited by respective inhibitory compounds based on their weight percent in the composition.

Units of enzyme per gram is calculated by conversion from units of enzyme inhibited in the reaction per quantity of compound present. Units of enzyme is defined as μmol of product (glucose or maltose) released at optimum condition per minute. A μmol of glucose (180 mol wt) or maltose (360 mol wt) based on units of enzyme inhibited are converted to grams of glucose or maltose which are easily converted to Kcal as 4 Kcal/gm.

For the alpha-glucosidase inhibition (AGH) contributed by the touchi extract, the results are reported as grams of glucose release blocked per gm inhibitor per minute.

For the alpha-amylase inhibition, contributed by the phaseolamin extract, the results are reported as grams of maltose release blocked per gm inhibitor per minute.

Touchi Extract Alone

If touchi extract is found to have 900 units of AGH inhibited per gram:
Then:

$$\frac{(900 \text{ μmol/min}) \times (180 \text{ μg/umol}) \times 10^{-6} \text{ g/ug}}{\text{units of enzyme mol wt glucose g conversion}} =$$

0.162 g glucose inhibition/min per gram touchi available

The potential for carbohydrate calories inhibited was then estimated based on a post-wprandial period of 180 minutes. For the above example:
0.162 g glucose inhibition/min×4 Kcal/gm carbohydrate× 180 min=116.6 Kcal inhibited per gram touchi available.

Phaseolamin Alone

If phaseolamin extract is found to have 6000 units of alpha-amylase inhibited per gram:
Then:

$$\frac{(6000 \text{ μmol/min}) \times (360 \text{ μg/umol}) \times 10 - 6 \text{ g/ug}}{\text{units of enzyme mol wt glucose g conversion}} =$$

2.16 g maltose inhibition/min per gram phaseolamin available

The potential for carbohydrate calories inhibited was then estimated based on a post-prandial period of 180 minutes. For the above example:
2.16 g glucose inhibition/min×4 Kcal/gm carbohydrate× 180 min=1555.2 Kcal inhibited per gram Phaseolamin available Composition If the composition is found to have 292 units of AGH inhibited per gram and 3167 units of alpha-amylase inhibited per gram:
Then:

$$\frac{(292 \text{ μmol/min}) \times (180 \text{ μg/umol}) \times 10 - 6 \text{ g/ug}}{\text{units of enzyme mol wt glucose g conversion}} =$$

0.05256 g glucose inhibition/min per gram composition 0.05256 g glucose inhibition/min×4 Kcal/gm carbohydrate×180 min=37.8 Kcal inhibited per gram composition available $$\frac{(3167 \text{ μmol/min}) \times (360 \text{ μg/umol}) \times 10 - 6 \text{ g/ug}}{\text{units of enzyme mol wt glucose g conversion}} =$$

1.14 g maltose inhibition/min per gram composition 1.14 g maltose inhibition/min×4 Kcal/gm carbohydrate× 180 min=820.8 Kcal inhibited per gram composition available Demonstrate Synergy If the 1 gram of composition contains 19% touchi by wt. and 32% phaseolamin by wt,
Theoretical calculation for AGH inhibition from touchi based on wt % of formula should be:

0.19 g×116.6 Kcal inhibited/gram=22.15 Kcal inhibited

Theoretical calculation for alpha-amylase inhibition from phaseolamin based on wt % of formula should be:

0.32 g×1555.2 Kcal inhibited/gram=497.7 Kcal inhibited

Illustration of Synergy as % Increase in Kcal Blocking Potential

| | Kcal blocking potential from touchi | Kcal blocking potential from Phaseolamin | Total Kcal blocking potential 1 g composition |
|---|---|---|---|
| 1000 mg composition | 37.8 | 820.8 | 858.6 Kcal |
| 190 mg touchi | 22.15 | 0 | |

| | Kcal blocking potential from touchi extract | Kcal blocking potential from Phaseolamin | |
|---|---|---|---|
| 320 mg Phaseolamin extract | 0 | 497.7 | |
| | | | Total Kcal blocking if two ingredients acted separately |
| | 22.15 | 497.7 | 519.85 Kcal |
| | | Difference in total Kcal blocking; Formula vs. separate ingredients alone (% improvement) | 338.75 Kcal |
| | | | 65% | i.e., for 1000 mg of the composition 37.8+820.8=858.6 Kcal 1000 mg of composition contains 190 mg touchi extract and 320 mg phaseolamin extract.

$$22.15 + 497.7 = 519.85 \text{ Kcal}$$

$$\frac{338.75}{519.85} * 100 = 65.16\% \text{ improvement}$$

The invention claimed is:

1. A nutritional supplement composition comprising an effective amount of a touchi extract, an effective amount of phaseolamin, and an acceptable carrier, wherein the nutritional supplement composition is substantially free of lipase inhibitor.

2. The nutritional supplement composition of claim 1 wherein the touchi extract comprises between about 13 and 27 weight percent of the nutritional supplement composition and the phaseolamin comprises between about 24 and 40 weight percent of the nutritional supplement composition.

3. The nutritional supplement composition of claim 1, wherein the touchi extract comprises a water extract of touchi.

4. The nutritional supplement composition of claim 3, further comprising a carminative.

5. The nutritional supplement composition of claim 4, wherein the carminative comprises organic parsley.

6. The nutritional supplement composition of claim 5 wherein the carrier comprises silicified microcrystalline cellulose.

7. The nutritional supplement composition of claim 1 comprising solid dosage units.

8. A nutritional supplement composition comprising touchi extract, phaseolamin, and an acceptable carrier, wherein the touchi extract comprises between about 18-19 weight percent of the nutritional supplement composition and the phaseolamin comprises between about 31-32 weight percent of the nutritional supplement composition.

9. The nutritional supplement composition of claim 8, wherein the carrier comprises silicified microcrystalline cellulose.

10. The nutritional supplement composition of claim 9 further comprising silicon dioxide.

11. The nutritional supplement composition of claim 8 comprising solid dosage units.

12. The nutritional supplement composition of claim 11 wherein the solid dosage units individually comprise about 100 mg touchi extract and about 166.67 mg phaseolamin.

* * * * *

UNITED STATES PATENT AND TRADEMARK OFFICE
CERTIFICATE OF CORRECTION

PATENT NO. : 7,354,606 B2
APPLICATION NO. : 11/131538
DATED : April 8, 2008
INVENTOR(S) : Mary A. Murray et al.

It is certified that error appears in the above-identified patent and that said Letters Patent is hereby corrected as shown below:

On the Title Page

In column 2, the 7th line under "OTHER PUBLICATIONS", after "*Rats and Humans*" delete "*Alter*" and substitute --*After*-- in its place.

In column 2, the 15th line under "OTHER PUBLICATIONS", after "*Alpha-Glucosidase*" delete "*Inhiboitor*" and substitute --*Inhibitor*-- in its place.

In column 2, the 16th line under "OTHER PUBLICATIONS", after "*Fermented*" delete "*Soybens*" and substitute --*Soybeans*-- in its place.

In column 2, the 18th line under "OTHER PUBLICATIONS", delete "Yamagami,," and substitute --Yamagami,-- in its place.

Page 2, column 1, the 36th line under "OTHER PUBLICATIONS", before "ISSN" delete "340-6,," and substitute --340-6,-- in its place.

Page 2, column 1, the 40th line under "OTHER PUBLICATIONS", delete "Dimitraiadis" and substitute --Dimitriadis-- in its place.

Page 2, column 2, the 9th line, after "International" delete "Journal" and substitute --Journal-- in its place.

Page 2, column 2, the 21st line, after "Service de" delete "Medeicine" and substitute "Médecine-- in its place.

Page 2, column 2, the 22nd line, after "Universitaire" delete "d' Angeres" and substitute --d'Angers-- in its place.

Page 2, column 2, the 28th line, after "*in NIDDM (non-*" delete "*inselin*" and substitute --*insulin*-- in its place.

UNITED STATES PATENT AND TRADEMARK OFFICE
CERTIFICATE OF CORRECTION

| | |
|---|---|
| PATENT NO. | : 7,354,606 B2 |
| APPLICATION NO. | : 11/131538 |
| DATED | : April 8, 2008 |
| INVENTOR(S) | : Mary A. Murray et al. |

It is certified that error appears in the above-identified patent and that said Letters Patent is hereby corrected as shown below:

On the Title Page (cont'd)

Page 2, column 2, the 40th line, before "(India)" delete "Microbial" and substitute --Microbiol-- in its place.

Signed and Sealed this

Twelfth Day of August, 2008

JON W. DUDAS
*Director of the United States Patent and Trademark Office*